(12) United States Patent
Gerlitz et al.

(10) Patent No.: US 6,841,371 B2
(45) Date of Patent: *Jan. 11, 2005

(54) PROTEIN C DERIVATIVES

(75) Inventors: Bruce Edward Gerlitz, Indianapolis, IN (US); Bryan Edward Jones, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/168,407

(22) PCT Filed: Jan. 19, 2001

(86) PCT No.: PCT/US01/00020

§ 371 (c)(1), (2), (4) Date: Jun. 20, 2002

(87) PCT Pub. No.: WO01/57193

PCT Pub. Date: Aug. 9, 2001

(65) Prior Publication Data

US 2003/0207435 A1 Nov. 6, 2003

Related U.S. Application Data

(60) Provisional application No. 60/179,801, filed on Feb. 2, 2000, and provisional application No. 60/189,197, filed on Mar. 14, 2000.

(51) Int. Cl.$^7$ .......................... C12N 9/64; A01N 61/00; A01N 25/00; A61K 38/28; A61K 35/00; A61K 35/14

(52) U.S. Cl. .............................. 435/226; 514/1; 514/4; 514/802; 514/822; 424/94.64; 530/381; 530/830

(58) Field of Search ............................. 435/226; 514/1, 514/4, 802, 822; 424/94.64; 530/381, 830

(56) References Cited

U.S. PATENT DOCUMENTS

| | | | |
|---|---|---|---|
| 4,992,373 A | 2/1991 | Bang et al. | |
| 5,196,322 A | 3/1993 | Bang et al. | |
| 5,270,178 A | 12/1993 | Gerlitz et al. | |
| 5,358,932 A | 10/1994 | Foster et al. | |
| 5,453,373 A | * 9/1995 | Gerlitz et al. ............... | 435/240 |
| 5,460,953 A | 10/1995 | Gerlitz et al. | |
| 5,837,843 A | 11/1998 | Smirnov et al. | |
| 5,847,085 A | 12/1998 | Esmon et al. | |
| 6,017,882 A | 1/2000 | Nelsestuen | |

FOREIGN PATENT DOCUMENTS

| | | |
|---|---|---|
| EP | 0 296 413 A2 | 9/1988 |
| EP | 0 354 504 A2 | 5/1989 |
| EP | 0 443 874 A2 | 2/1991 |
| JP | 03 072877 A | 3/1991 |
| WO | WO 91/09960 | 7/1991 |
| WO | WO 98/44000 | 10/1998 |
| WO | WO 99/20767 | 4/1999 |
| WO | WO 00/66754 | 11/2000 |
| WO | WO 01/36462 A2 | 5/2001 |
| WO | WO 01/57193 | 8/2001 |
| WO | WO 01/59084 A1 | 8/2001 |
| WO | WO 01/72328 A3 | 10/2001 |
| WO | WO 02/070681 A1 | 9/2002 |

OTHER PUBLICATIONS

U.S. patent application Ser. No. 09/467,591, Nelsestuen, Feb. 3, 2000.

U.S. patent application Ser. No. 09/803,810, Nelsestuen, Mar. 12, 2001.

Database Swall Online!, "Vitamin K–dependent protein C precursor" European Bioinformatics Institute & Swiss Institute for Bioinformatics, 1986.

Grinnell B, et al., "Glycosylation of Human protein C Affects Its Secretion, Processing, Functional Activities, and Activation by Thrombin", Journal of Biological Chemistry, vol. 226, No. 15, 1991; pp. 9778–9785.

Rezaie AR, et al., "Conversion of Glutamic Acid 192 to Glutamine in Activated Protein C Changes the Substrate Specificity and Increases Reactivity toward Macromolecular Inhibitors*", Journal of Biological Chemistry, vol. 268, No. 27, 1993, pp. 19943–19948.

Mather T, et al., "The 2.8A crystal structure of Gla–domain-less activated protein C", The Embo Journal, vol. 15, No. 24, 1996, pp. 6822–6831.

Tsiang M, et al., "Protein Engineering Thrombin for Optimal Specificity and Potency of Anticoagulant Activity in Vivo", Biochemistry, vol. 35, No. 51, 1996, pp. 16449–16457.

Rezaie AR, "Role of Residue 99 at the S2 Subsite of Factor Xa and Activated Protein C in Enzyme Specificity", Journal of Biological Chemistry, The American Socirty of Biological Chemists, Inc., vol. 271, No. 39, 1996, pp. 23807–23814.

Kurz K, et al., "Antithrombic Efficacy in the Guinea Pig of a Derivative of Human Protein C With Enhanced Activation by Thrombin", Blood, vol. 89, No. 2, 1997, pp. 534–540.

Shen L, et al., "Enhancing the Activity of Protein C by Mutagenesis To Improve the Membrane–Binding Site: Studies Related to Proline–10" Biochemistry, American Chemical Society, vol. 36, No. 51, 1997, pp. 16025–16031.

Shen L, et al., "Enhancement of Human Protein C Function by Site–directed Mutagenesis of the y–Carboxyglutamic Acid Domain", Journal of Biological Chemistry, American Society of Biological Chemists, vol. 273, No. 47, 1998, pp. 31086–31091.

(List continued on next page.)

Primary Examiner—Rebecca E. Prouty
Assistant Examiner—Sheridan Swope
(74) Attorney, Agent, or Firm—Thomas E. LaGrandeur; Brian P. Barrett; Lynn D. Apelgren

(57) ABSTRACT

Novel human protein C derivatives are described. These derivatives have increased anti-coagulation activity and resistance to inactivation by serpins, compared to wild-type protein C and retain the biological activity of the wild-type human protein D. These derivatives will require either less frequent administration and/or smaller dosage than wild-type human protein C in the treatment of acute coronary syndromes, vascular occlusive disorders, hyper coagulable states, thrombotic disorders and disease states predisposing to thrombosis.

23 Claims, 1 Drawing Sheet

OTHER PUBLICATIONS

McDonald J, et al., "Comparison of Naturally Occuring Vitamin K–Dependent Proteins: Correlation of Amino Acid Sequences and Membrane Binding Properties Suggests a Membrane Contact Site", *Biochemistry*, vol. 36, No. 17, 1997, pp. 5120–5127.

Zhang L, et al., "The Contributions of Individual γ–Carboxyglutamic Acid Residue in the Calcium–dependent Binding of Recombinant Human Protein C to Acidic Phospholipid Vesicles", *The Journal of Biological Chemistry*, vol. 268, No. 16, 1993, pp. 12040–12045.

U.S. patent application Ser. No. 09/719,911, Gerlitz et al.

U.S. patent application Ser. No. 10/129,893, Gerlitz et al.

U.S. patent application Ser. No. 10/182,263, Gerlitz et al.

* cited by examiner

PROTEIN C DERIVATIVES

This application claims priority of Provisional Application Ser. No. 60/179,801 filed Feb. 2, 2000 and Ser. No. 60/189,197 filed Mar. 14, 2000.

This invention relates to novel polynucleotides, polypeptides encoded by them and to the use of such polynucleotides and polypeptides. More specifically, the invention relates to human protein C derivatives with resistance to serpin inactivation and increased anti-coagulant activity as compared to wild-type activated protein C, to their production, and to pharmaceutical compositions comprising these human protein C derivatives.

BACKGROUND

Protein C is a serine protease and naturally occurring anti-coagulant that plays a role in the regulation of hemostasis by inactivating Factors $V_a$ and $VIII_a$ in the coagulation cascade. Human protein C is made in vivo as a single polypeptide of 461 amino acids. This polypeptide undergoes multiple post-translational modifications including, 1) cleavage of a 42 amino acid signal sequence; 2) cleavage of lysine and arginine residues (positions 156 and 157) to make a 2-chain inactive precursor or zymogen (an 155 amino acid residue light chain attached via a disulfide bridge to a 262 amino acid residue heavy chain); 3) vitamin K-dependent carboxylation of nine glutamic acid residues located within the amino-terminal 45 residues (gla-domain); and, 4) carbohydrate attachment at four sites (one in the light chain and three in the heavy chain). Finally, the 2-chain zymogen may be activated by removal of a dodecapeptide at the N-terminus of the heavy chain, producing activated protein C (aPC) possessing greater enzymatic activity than the 2-chain zymogen.

Blood coagulation is a highly complex process regulated by the balance between pro-coagulant and anti-coagulant mechanisms. This balance determines a condition of either normal hemostasis or abnormal pathological thrombus generation and the progression, for example, of coronary thrombosis leading to acute coronary syndromes (ACS; e.g. unstable angina, myocardial infarction). Two major factors control this balance; the generation of fibrin and the activation and subsequent aggregation of platelets, both processes controlled by the generation of the enzyme thrombin, which occurs following activation of the clotting cascade. Thrombin, in complex with thrombomodulin, also functions as a potent anti-coagulant since it activates protein C zymogen to aPC, which in turn inhibits the generation of thrombin. Thus, through the feedback regulation of thrombin generation via the inactivation of Factors Va and VIIIa, aPC functions as perhaps the most important down-regulator of blood coagulation resulting in protection against thrombosis. In addition to anti-coagulation, aPC has anti-inflammatory effects and exerts profibrinolytic properties that facilitate clot lysis.

Arterial thrombosis occurs in ACS in response to endothelial injury, typically as a result of a disruption of lipid-rich plaque. The initial phases of this response involve platelet adhesion, activation, and assembly of various pro-coagulants at the site of injury and on the surfaces of activated platelets. The resultant elaboration of thrombin generation plays a critical role in the progression of thrombus formation: both by fibrin deposition, and by platelet activation, thus potentiating the activation of the coagulation system. Traditional (e.g. unfractionated heparin [UFH]) and current (e.g. low-molecular weight heparin [LMWH]) anti-coagulant therapies for ACS rely on the inhibition of thrombin and/or Factor Xa (e.g. the heparins inactivate both thrombin and Xa by dramatically stimulating their interaction with anti-thrombin-III). However, due to steric constraints, these agents are not as effective in inhibiting clot-bound Xa or thrombin. The ability of aPC to target and to irreversibly inactivate the clot-bound Xa/Va complex attenuates local thrombin generation and the progression of thrombosis. Thus, aPC provides an advantage compared to current inhibitors of thrombin or Xa since the effect of decreased thrombin generation will persist after concentrations of aPC have decayed.

The critical role of aPC in controlling hemostasis is also exemplified by the increased rate of thrombosis in heterozygous deficiency, protein C resistance (e.g., due to the common Factor V Leiden mutation) and the fatal outcome of untreated homozygous protein C deficiency. Plasma-derived and recombinantly produced aPC have been shown to be effective and safe anti-thrombotic agents in a variety of animal models of both venous and arterial thrombosis.

Protein C levels have also been shown to be abnormally low in the following diseases and conditions: disseminated intravascular coagulation (DIC)[Fourrier, et al., *Chest* 101:816–823, 1992], sepsis [Gerson, et al., *Pediatrics* 91:418–422, 1993], major trauma/major surgery [Thomas, et al., *Am J. Surg.* 158:491–494, 1989], burns [Lo, et al., *Burns* 20:186–187 (1994)], adult respiratory distress syndrome (ARDS)[Hasegawa, et al., *Chest* 105(1):268–277, 1994], and transplantations [Gordon, et al., *Bone Marrow Trans.* 11:61–65 (1993)]. In addition, there are numerous diseases with thrombotic abnormalities or complications that aPC may be useful in treating, such as: heparin-induced thrombocytopenia (HIT) [Phillips, et al., *Annals of Pharmacotherapy* 28: 43–45, 1994], sickle cell disease or thalassemia [Karayalcin, et al., *The American Journal of Pediatric Hematology/Oncology* 11(3):320–323, 1989], viral hemorrhagic fever [Lacy, et al., *Advances in Pediatric Infectious Diseases* 12:21–53, 1997], thrombotic thrombocytopenic purpura (TTP) and hemolytic uremic syndrome (HUS) [Moake, *Seminars in Hematology* 34(2):83–89, 1997]. In addition, aPC in combination with Bactericidal Permeability Increasing Protein (BPI) may be useful in the treatment of sepsis [Fisher, et al., *Crit. Care Med.* 22(4):553–558, 1994].

It is well established that platelet inhibition is efficacious in both prevention and treatment of thrombotic disease. However, the use of anti-platelet agents, such as aspirin, increase the risk of bleeding, which limits the dose of the agent and duration of treatment. The combination of aPC and anti-platelet agents results in a synergy that allows the reduction of the dosages of both aPC and the anti-platelet agent(s). The reduction of the dosages of the agents in combination therapy in turn results in reduced side effects such as increased bleeding often observed in combination anti-coagulant/anti-platelet therapy.

Various methods of obtaining protein C from plasma and producing protein C, aPC and protein C/aPC polypeptides through recombinant DNA technology are known in the art and have been described. See e.g., U.S. Pat. Nos. 4,775,624 and 5,358,932. Despite improvements in methods to produce aPC through recombinant DNA technology, aPC and polypeptides thereof are difficult and costly to produce.

Unlike the zymogen protein C, activated protein C has an extremely short half-life. A major reason for the short half-life is that blood levels of aPC are regulated by molecules known as serpins (Serine Protease Inhibitors), which covalently bind to aPC forming an inactive serpin/aPC complex. The serpin/aPC complexes are formed when aPC binds and proteolytically cleaves a reactive site loop within the serpin; upon cleavage, the serpin undergoes a conformational change irreversibly inactivating aPC. The serpin/aPC complex is then eliminated from the bloodstream via hepatic receptors for the serpin/aPC complex. As a result, aPC has a relatively short half-life compared to the zymogen; approximately 20 minutes for aPC versus approximately 10 hours for human protein C zymogen (Okajima, et al., *Thromb Haemost* 63(1):48–53, 1990).

Therefore, an aPC derivative exhibiting resistance to serpin inactivation, while maintaining the desirable biological activities of aPC (e.g., anti-coagulant, fibrinolytic, and anti-inflammatory activities), provides a compound that has an increased plasma half-life and is effectively more potent than the parent compound, requiring substantially reduced dosage levels for therapeutic applications. The potency advantages are especially important in disease states in which serpin levels are elevated.

SUMMARY

Through scientific experimentation, analysis, and innovation the present inventors identified serpin and protein C binding sites essential to formation of serpin/aPC complexes. Targeted amino acid residues in the aPC molecule were modified and surprisingly inhibited formation of the serpin/aPC complex (the complex which irreversibly inactivates aPC) while at the same time retaining the specificity of the aPC derivative for aPC's natural substrates (e.g. Factor Va and VIIIa). Additionally, it was found that inhibition of serpin/human aPC derivative binding occurred by substituting one or more of the following amino acids: 194 (Leu), 195 (Ala), 228 (Leu), 249 (Tyr), 254 (Thr), 302 (Tyr), and 316 (Phe) of SEQ ID NO: 1 with an amino acid(s) selected from Ser, Ala, Thr, His, Lys, Arg, Leu, Asn, Asp, Glu, Gly, and Gln, provided that position 194 is not substituted with Leu and position 254 is not substituted with Thr.

Additionally, an aPC derivative exhibiting increased anti-coagulant activity, while maintaining the other biological activities of aPC (e.g., fibrinolytic, and anti-inflammatory activities), provides a compound that is effectively more potent than the parent compound, requiring substantially reduced dosage levels for therapeutic applications.

Enhancement of human protein C calcium and membrane binding activity by site-directed mutagenesis of the gla-domain has been reported by several investigators, for example, Shen et al. (*J Biol. Chem.*, 273(47) 31086–91, 1998) and Shen et al. (*Biochemistry*, 36(51) 16025–31, 1997). Through continued scientific experiments, analysis, and innovation, the present inventors identified specific sites and modified targeted amino acid residues in the gla-domain of the aPC molecule. Surprisingly, it was observed that increased anti-coagulant activity of the aPC derivative occurred when specific site-directed mutations were performed. In particular, substitutions at amino acid positions: 10 (His), 11 (Ser), 12 (Ser), 32 (Gln), and 33 (Asn) of SEQ ID NO: 1, alone or in combinations thereof were found to have increased anti-coagulant activity when compared to wide-type aPC.

Accordingly, the present invention describes novel human protein C derivatives. These human protein C derivatives retain the important biological activity of the wild-type protein C and have greater anti-coagulant activity and have longer half-lives in human blood than wild-type aPC. Therefore, these compounds provide various advantages, e.g. less frequent administration and/or smaller dosages and thus a reduction in the overall cost of production and therapy. Furthermore, these compounds exhibit an advantage over traditional anti-coagulant therapies in disease states such as ACS. Importantly, the increases in human protein C derivative anti-coagulant activity and resistance to serpin inactivation may be achieved preferably via two to six amino acid substitutions, which are less likely to be immunogenic in comparison to molecules which contain more than six amino acid substitutions (U.S. Pat. No. 5,358,932; Holly, et al., *Biochemistry* 33:1876–1880, 1994).

DETAILED DESCRIPTION

Figure 1:
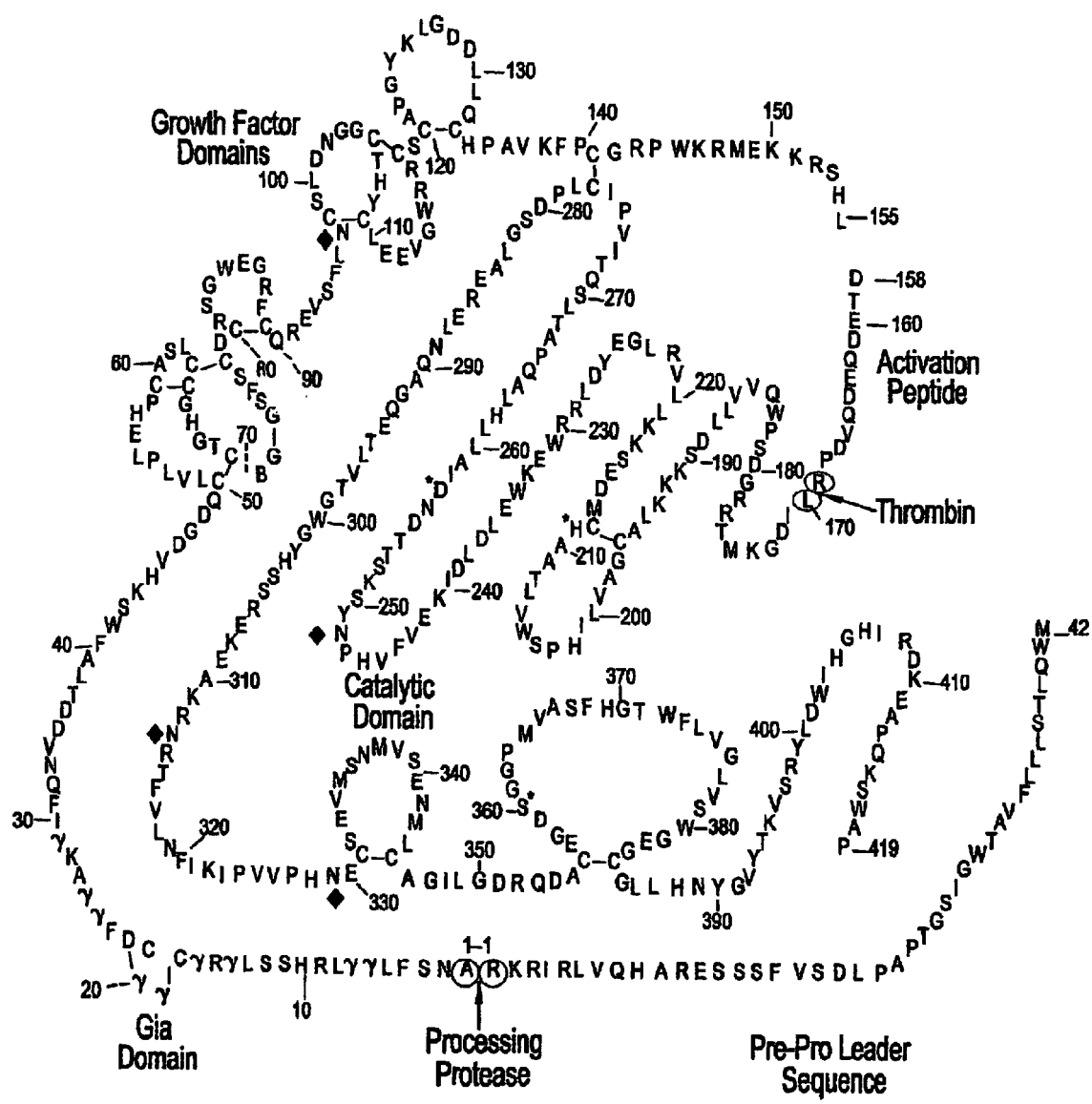
FIG. 1 is a schematic representation of the amino acid sequence of the heavy and light chains of the protein C molecule, including the pre-pro leader (signal) sequence.

The present invention provides a human protein C derivative comprising SEQ ID NO: 1 containing at least two of the following amino acid substitutions:

His at position 10 is substituted with Gln; Ser at position 11 is substituted with Gly; Ser at position 12 is substituted with Lys; Gln at position 32 is substituted with Glu; Asn at position 33 is substituted with Asp or Phe; and, the amino acid at position 194, 195, 228, 249, 254, 302, or 316 is substituted with an amino acid selected from Ser, Ala, Thr, His, Lys, Leu, Arg, Asn, Asp, Glu, Gly, and Gln.

The present invention also provides recombinant DNA molecules encoding the human protein C derivatives of the present invention, in particular those comprising SEQ ID NOS: 7, 8, 9, and 10.

Another aspect of the present invention provides protein sequences of the above mentioned human protein C derivatives, particularly those comprising SEQ ID NOS: 3, 4, 5, and 6, and the activated forms of these human protein C derivatives.

The present invention further comprises methods of treating vascular occlusive disorders and hypercoagulable states including: sepsis, disseminated intravascular coagulation, purpura fulminans, major trauma, major surgery, burns, adult respiratory distress syndrome, transplantations, deep vein thrombosis, heparin-induced thrombocytopenia, sickle cell disease, thalassemia, viral hemorrhagic fever, thrombotic thrombocytopenic purpura, and hemolytic uremic syndrome.

Another aspect of the invention comprises treating the diseases and conditions caused or resulting from protein C deficiency as defined herein.

The invention further provides treating the above-mentioned diseases and conditions by administering to a patient in need thereof a pharmaceutically effective amount of a human protein C derivative.

The invention further provides treating the above mentioned diseases and conditions employing the activated form of the above-identified human protein C derivatives.

Another embodiment of the present invention is a method of treating sepsis comprising the administration to a patient in need thereof a pharmaceutically effective amount of a human protein C derivative of this invention in combination with bacterial permeability increasing protein.

Another embodiment of the present invention is a method of treating thrombotic disorders which comprises of administering to a patient in need thereof a pharmaceutically effective amount of a human protein C derivative of this invention in combination with an anti-platelet agent.

Another embodiment of the present invention is a method of treating acute arterial thrombotic occlusion, thromboembolism, or stenosis in coronary, cerebral or peripheral arteries or in vascular grafts comprising: administering to a patient in need thereof a pharmaceutically effective amount of a human activated protein C derivative in combination with a thrombolytic agent.

Yet another embodiment of the present invention is a method of treating human patients with genetically predisposed prothrombotic disorders which comprises administering gene therapy to said patients with a recombinant DNA molecule encoding a protein C derivative. Examples of genetically predisposed prothrombotic disorders are protein C deficiency, Factor V Leiden mutation, and prothrombin gene G20210A mutation.

The present invention also provides a pharmaceutical composition comprising a pharmaceutically acceptable carrier or diluent and a human protein C derivative of this invention.

The present invention also provides for the use of the human activated protein C derivatives of this invention for the manufacture of a medicament for the treatment of the above-mentioned indications.

Methods and aspects of producing the novel human protein derivatives are also an aspect of this invention.

For purposes of the present invention, as disclosed and claimed herein, the following terms are as defined below.

Anti-platelet agent—one or more agents alone or in combination which reduces the ability of platelets to aggregate. Agents understood and appreciated in the art include those cited in, for example, Remington, *The Science and Practice of Pharmacy*, Nineteenth Edition, Vol II, pages 924–25, Mack Publishing Co., herein incorporated by reference. Such agents include but are not limited to aspirin (ASA), clopidogrel, ReoPro® (abciximab), dipyridamole, ticlopidine and IIb/IIIa antagonists.

Zymogen—protein C zymogen, as used herein, refers to secreted, inactive forms, whether one chain or two chains of protein C or derivatives thereof. Cleavage of lysine and arginine residues (positions 156 and 157) results in a 2-chain (heavy and light) inactive zymogen.

Activated protein C refers to the activated form of protein C zymogen which is produced after by removal of a dodecapeptide at the N-terminus of the heavy chain, producing activated protein C.

Activated protein C or aPC refers to recombinant aPC. aPC includes and is preferably recombinant human aPC although aPC may also include other species having protein C proteolytic, amidolytic, esterolytic, and biological (anti-coagulant, anti-inflammatory, or pro-fibrinolytic) activities.

Human protein C derivative(s) refers to the recombinantly produced derivatives of this invention that differ from wild-type human protein C but when activated retain the essential properties i.e., proteolytic, amidolytic, esterolytic, and biological (anti-coagulant, anti-inflammatory, pro-fibrinolytic activities). The definition of human protein C derivatives as used herein also includes the activated form of the above-identified human protein C derivatives.

Treating—describes the management and care of a patient for the purpose of combating a disease, condition, or disorder whether to eliminate the disease, condition, or disorder, or prophylactically to prevent the onset of the symptoms or complications of the disease, condition, or disorder.

Continuous infusion—continuing substantially uninterrupted the introduction of a solution or suspension into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Unit dosage form—refers to physically discrete units suitable as unitary dosages for human subjects, each unit containing a predetermined quantity of active material calculated to produce the desired therapeutic effect, in association with a suitable pharmaceutical excipient.

Hypercoagulable states—excessive coagulability associated with disseminated intravascular coagulation, prethrombotic conditions, activation of coagulation, or congenital or acquired deficiency of clotting factors such as aPC.

Protein C deficiency—protein C deficiency as used herein can be congenital or acquired. For either type, the protein C level in circulation is below the lower limit of the normal range. Skilled artisans realize that the normal range is established by a standard protocol utilizing FDA approved equipment and diagnostic kits for determining protein C levels.

Pharmaceutically effective amount—a therapeutically efficacious amount of a pharmaceutical compound. The particular dose of the compound administered according to this invention will, of course, be determined by the attending physician evaluating the particular circumstances surrounding the case, including the compound administered, the particular condition being treated, the patient characteristics and similar considerations.

Acute coronary syndromes—clinical manifestations of coronary atherosclerosis complicated by coronary plaque rupture, superimposed coronary thrombosis, and jeopardized coronary blood flow resulting in coronary ischemia and/or myocardial infarction. The spectrum of acute coronary syndromes includes unstable angina, non-Q-wave (i.e., non-ST-segment elevation) myocardial infarction, and Q-wave (i.e., ST-segment elevation) myocardial infarction.

Gene Therapy—A therapeutic regime which includes the administration of a vector containing DNA encoding a therapeutic protein, directly to affected cells where the therapeutic protein will be produced. Target tissue for gene delivery include, for example, skeletal muscle, vascular smooth muscle, and liver. Vectors include, for example, plasmid DNA, liposomes, protein-DNA conjugates, and vectors based on adenovirus or herpes virus. Gene therapy has been described, for example, by Kessler et al., PNAS, USA, 93:14082–87, 1996.

Thrombotic disorders—a disorder relating to, or affected with the formation or presence of a blood clot within a blood vessel. Such disorders include, but are not limited to, stroke, abrupt closure following angioplasty or stent placement, and thrombosis as a result of peripheral vascular surgery.

Purpura fulminans—ecchymotic skin lesions, fever, hypotension associated with bacterial sepsis, viral, bacterial or protozoan infections. Disseminated intravascular coagulation is usually present.

Tissue factor pathway inhibitor (TFPI)—refers to naturally or recombinant forms of TFPI. This protein is believed to block tissue-mediated clotting in small blood vessels, which potentially leads to organ failure and death.

Serpin—any of a group of structurally related proteins that typically are serine protease inhibitors whose inhibiting activity is conferred by a reactive site in a highly variable and mobile peptide loop and that include but are not limited to protein C inhibitor (PCI) and aα₁-antitrypsin (α₁-AT).

Inhibitor recognition sequence S2: the 2$^{nd}$ residue N-terminal to the cleavage site of PCI or α₁-AT.

Inhibitor recognition sequence S3': the 3$^{rd}$ residue C-terminal to the cleavage site of PCI or α₁-AT.

Inhibitor recognition sequence S4': the 4$^{th}$ residue C-terminal to the cleavage site of PCI or α₁-AT.

Wild-type protein C—the type of protein C that predominates in a natural population of humans in contrast to that of natural or laboratory mutant polypeptide forms of protein C.

Bactericidal permeability increasing protein—includes naturally and recombinantly produced bactericidal permeability increasing (BPI) protein; natural, synthetic, and recombinant biologically active polypeptide fragments of BPI protein; biologically active polypeptide variants of BPI protein or fragments thereof, including hybrid fusion proteins and dimers; biologically active variant analogs of BPI protein or fragments or variants thereof, including cysteine-substituted analogs; and BPI-derived peptides. The complete amino acid sequence of human BPI, as well as the nucleotide sequence of DNA encoding BPI have been elucidated by Gray, et al., 1989, *J. Biol. Chem* 264:9505. Recombinant genes encoding and methods for expression of BPI proteins, including BPI holoprotein and fragments of BPI are disclosed in U.S. Pat. No. 5,198,541, herein incorporated by reference.

The amino acid abbreviations are accepted by the United States Patent and Trademark Office as set forth in 37 C.F.R. 1.822 (d)(1) (1998).

The present invention provides human protein C derivatives, including activated forms thereof, which have increased anti-coagulant activity and resistance to serpin inactivation as compared to wild-type protein C. The activated form of aPC or human aPC derivatives may be produced by activating recombinant human protein C zymogen or recombinant human protein C derivative zymogen in vitro or by direct secretion of the activated form of protein C. The means by which the activation occurs is not critical and the process aspects of this invention include any and all means of activation. Human protein C derivatives may be produced in eukaryotic cells, transgenic animals, or transgenic plants, including, for example, secretion from human kidney 293 cells or AV12 cells as a zymogen, then purified and activated by techniques known to the skilled artisan.

Preferred human protein C derivatives of the present invention include S11G:Q32E:N33D:L194S, S11G:Q32E:N33D:L194S:T254S, H10Q:S11G:Q32E:N33D:L194S, H10Q:S11G:Q32E:N33D:L194S:T254S and activated forms thereof.

Human protein C derivative S11G:Q32E:N33D:L194S contains a glycine residue at position 11 instead of a serine residue normally found at this position, a glutamic acid residue at position 32 instead of the glutamine residue normally found at this position an aspartic acid residue at position 33 instead of the asparagine residue normally found at this position and a serine at position 194 instead of the leucine residue normally found at this position. Other preferred amino acid substitutions at position 194 include Ala, Arg, Asn, Asp, Glu, Gly, Ser, Lys, Gln, Leu, Thr, and His.

Human protein C derivative S11G:Q32E:N33D:L194S:T254S contains a glycine residue at position 11 instead of a serine residue normally found at this position, a glutamic acid residue at position 32 instead of the glutamine residue normally found at this position; an aspartic acid residue at position 33 instead of the asparagine residue normally found at this position, a serine residue at position 194 instead of the leucine residue normally found at this position, and a serine residue at position 254 instead of a threonine residue normally found at this position. Other preferred amino acid substitutions at positions 194 and 254 include Ala, Arg, Asn, Asp, Glu, Gly, Ser, Lys, Gln, Leu, Thr, and His, provided position 11 is not Ser, position 32 is not Gln, 33 is not Asn, 194 is not Leu, and 254 is not Thr.

Human protein C derivative H10Q:S11G:Q32E:N33D:L194S contains a glutamine residue at position 10 instead of the histidine residue normally found at that position, a glycine residue at position 11 instead of the serine residue normally found at this position, a glutamic acid residue at position 32 instead of the glutamine residue normally found at this position an aspartic acid residue at position 33 instead of the asparagine residue normally found at this position, and a serine residue at position 194 instead of the leucine residue normally found at this position. With the teachings of the present invention, it is apparent to one with skill in the art that other amino acid substitutions at these positions impart increased anti-coagulant activity and resistance to serpin inactivation in the resulting derivative molecule. Examples of such amino acid substitutions include Ala, Arg, Asn, Asp, Glu, Gly, Ser, Lys, Gln, Leu, Thr, and His.

Human protein C derivative $H_{10}$Q:S11G:Q32E:N33D:L194S:T254S contains a glutamine residue at position 10 instead of the histidine residue normally found at that position, a glycine residue at position 11 instead of the serine residue normally found at this position, a glutamic acid residue at position 32 instead of the glutamine residue normally found at this position an aspartic acid residue at position 33 instead of the asparagine residue normally found at this position, a serine residue at position 194 instead of the leucine residue normally found at this position, and a serine residue at position 254 instead of the threonine residue normally found at this position. Other preferred amino acid substitutions at positions 194 and 254 include Ala, Arg, Asn, Asp, Glu, Gly, Ser, Lys, Gln, Leu, Thr, and His.

Further embodiments of the present invention include human protein C derivatives: S12K:L194S, S12K:L194S:T254S, H10Q:S11G:S12K:L194S, H10Q:S11G:S12K:L194S:T254S, S11G:L194S, H10Q:S11G:L194S, S11G:L194S:T254S, H10Q:S11G:L194S, S11G:L194S:T254S, and activated forms thereof which have increased anti-coagulant activity and resistance to serpin inactivation as compared to wild-type activated protein C.

Human protein C derivative S12K:L194S contains a lysine residue at position 12 instead of the serine residue normally found at this position and a serine residue at position 194 instead of the leucine residue normally found at this position. Other preferred amino acid substitutions at position 194 include Ala, Arg, Asn, Asp, Glu, Gly, Ser, Lys, Gln, Leu, Thr, and His.

Human protein C derivative S12K:L194S:T254S contains a lysine residue at position 12 instead of the serine residue normally found at this position, a serine residue at position 194 instead of the leucine residue normally found at this position, and a serine residue at position 254 instead of a threonine residue normally found at this position. Other preferred such amino acid substitutions at position 194 and 254 include Ala, Arg, Asn, Asp, Glu, Gly, Ser, Lys, Gln, Leu, Thr, and His.

Human protein C derivative H10Q:S11G:S12K:L194S contains a glutamine residue at position 10 instead of the histidine residue normally found at that position, a glycine residue at position 11 instead of the serine residue normally found at this position, a lysine residue at position 12 instead of the serine residue normally found at this position and a serine at residue 194 instead of the leucine residue normally found at this position. Other preferred amino acid substitutions at position 194 include Ala, Arg, Asn, Asp, Glu, Gly, Ser, Lys, Gln, Leu, Thr, and His.

Human protein C derivative H10Q:S11G:S12K:L194S:T254S, preferably contains a glutamine residue at position 10 rather than a histidine residue normally found at this position, a glycine residue at position 11 instead of the serine residue normally found at this position, a lysine residue at 12 instead of the serine residue normally found at this position, a serine residue at position 194 instead of the leucine residue normally found at this position and a serine residue at position 254 instead of the threonine residue normally found at this position. Other preferred amino acid substitutions for positions 194 and 254 include, Ala, Arg, Asn, Asp, Glu, Gly, Ser, Lys, Gln, Leu, Thr, and His.

Human protein C derivative S11G:L194S contains a glycine residue at position 11 instead of the serine residue normally found at this position and a serine residue at position 194 instead of the leucine residue normally found at this position. Other preferred amino acid substitutions for position 194 include Ala, Arg, Asn, Asp, Glu, Gly, Ser, Lys, Gln, Leu, Thr, and His.

Human protein C derivative H10Q:S11G:L194S, preferably contains a glutamine residue at position 10 rather than a histidine residue normally found at this position, a glycine residue at position 11 instead of the serine residue normally found at this position, and a serine residue at position 194 instead of the leucine residue normally found at this position. Other preferred amino acid substitutions for position include Ala, Arg, Asn, Asp, Glu, Gly, Ser, Lys, Gln, Leu, Thr, and His.

Human protein C derivative S11G:L194S:T254S contains a glycine residue at position 11 instead of the serine residue normally found at this position, a serine residue at position 194 instead of the leucine residue normally found at this position, and a serine residue at position 254 instead of the threonine residue normally found at this position. Other preferred such amino acid substitutions for positions 194 and 254 include Ala, Arg, Asn, Asp, Glu, Gly, Ser, Lys, Gln, Leu, Thr, and His.

Additional preferred embodiments of the present invention include protein C derivatives: S11G:Q32E:L194S, S11G:Q32E:L194S:T254S, S11G:Q32E:N33F:L194S, and S11G:Q32E:N33F:L194S:T254S, and activated forms thereof which have increased anti-coagulation activity and resistance to serpin inactivation as compared to wild-type activated protein C.

Human protein C derivative S11G:Q32E:L194S: contains a glycine residue at position 11 instead of the serine residue normally found at this position, a glutamic acid residue at position 32 instead of the glutamine residue normally found at this position and a serine residue at position 194 instead of the leucine residue normally found at this position. Other preferred such amino acid substitutions at position 194 include Ala, Arg, Asn, Asp, Glu, Gly, Ser, Lys, Gln, Leu, Thr, and His.

Human protein C derivative S11G:Q32E:L194S:T254S contains a glycine residue at position 11 instead of the serine residue normally found at this position, a glutamic acid residue at position 32 instead of the glutamine residue normally found at this, a serine residue at position 194 instead of the leucine residue normally found at this position, and a serine residue at position 254 instead of the threonine residue normally found at this position. Other preferred such amino acid substitutions at positions 194 and 254 include Ala, Arg, Asn, Asp, Glu, Gly, Ser, Lys, Gln, Leu, Thr, and His.

Human protein C derivative S11G:Q32E:N33F:L194S contains a glycine residue at position 11 instead of the serine residue normally found at this position, a glutamic acid residue at position 32 instead of the glutamine residue normally found at this position a phenylalanine residue at position 33 instead of the asparagine residue normally found at this position, and a serine residue at position 194 instead of the leucine residue normally found at this position. Other preferred amino acid substitutions at position 194 include Ala, Arg, Asn, Asp, Glu, Gly, Ser, Lys, Gln, Leu, Thr, and His.

Human protein C derivative S11G:Q32E:N33F:L194S:T254S contains a glycine residue at position 11 instead of the serine residue normally found at this position, a glutamic acid residue at position 32 instead of the glutamine residue normally found at this position a phenylalanine residue at position 33 instead of the asparagine residue normally found at this position, a serine residue at position 194 instead of the leucine residue normally found at this position, and a serine residue at position 254 instead of the threonine residue normally found at this position. Other preferred amino acid substitutions at positions 194 and 254 include Ala, Arg, Asn, Asp, Glu, Gly, Ser, Lys, Gln, Leu, Thr, and His.

In addition, human protein C derivatives of the present invention include additional deletions, additions, or substitutions of amino acid residues of the protein C derivatives described above, but which result in changes that do not effect the basic characteristics of this invention. Amino acid substitutions may be made on the basis of similarity in polarity, charge, solubility, hydrophobicity, hydrophilicity, and/or the amphipathic nature of the residues involved. Thus, the derivatives of the present invention include derivatives having an amino acid sequence that vary from SEQ ID NOS: 3, 4, 5, and 6, by conservative substitutions i.e., those that substitute a residue with another of like characteristics. Typical substitutions are among Ala, Val, Leu and Ile; among Ser and Thr; among the acidic residues Asp and Glu; among Asn and Gin; and among the basic residues Lys and Arg; or aromatic residues Phe and Tyr. Other derivatives are those in which several, 5–10, 1–5, or 1–2 amino acids are substituted, deleted, or added in any combination. A preferred embodiment is based on SEQ ID NO: 1 includes the addition of the 42 amino acid signal peptide (pre-pro leader) sequence as illustrated in FIG. 1 and shown in SEQ ID NO: 2.

Preferably, the human protein C derivatives of the present invention are not further substituted or modified. That is, substitutions are limited to the derivatives of the present invention.

The invention also provides DNA compounds for use in making the human protein C derivatives. These DNA compounds comprise the coding sequence for the light chain of human protein C zymogen or human protein C derivative zymogen positioned immediately adjacent to, downstream of, and in translational reading frame with the prepropeptide sequence of human protein C zymogen or human protein C derivative zymogen. The DNA sequences preferably encode the Lys-Arg dipeptide which is processed during maturation of the protein C molecule, the activation peptide and the heavy chain of the human protein C derivative. Thus, the human protein C derivatives of the present invention are variant or mutant polypeptides which contain at least 2, preferably 2 to 6 amino acids, which differ from the wild-type protein C sequence identified as SEQ ID NO: 1 (which does not contain the 42 amino acid signal sequence) or the corresponding wild-type amino acid in SEQ ID NO: 2 (which contains the 42 amino acid signal sequence). Thus, one skilled in the art recognizes that a human protein C derivative which differs from the amino acid sequence of the wild-type protein C sequence identified as SEQ ID NO: 1 inherently corresponds to the wild-type protein C sequence identified as SEQ ID NO: 2 at the amino acid position determined after removal of the 42 amino acid signal sequence. Furthermore, one skilled in the art recognizes that prior to activation, the cleavage of the lysine and arginine residues (positions 156 and 157) occurs.

Those skilled in the art will recognize that, due to the degeneracy of the genetic code, a variety of DNA compounds can encode the derivatives described above. U.S. Pat. No. 4,775,624, the entire teaching of which is herein incorporated by reference, discloses the wild-type form of the human protein C molecule. The skilled artisan could readily determine which changes in the DNA sequences could encode the exact derivatives as disclosed herein. The invention is not limited to the specific DNA sequences disclosed. Consequently, the construction described below and in the accompanying Examples for the preferred DNA compounds are merely illustrative and do not limit the scope of the invention.

All of the DNA compounds of the present invention were prepared by the use of site-directed mutagenesis to change particular positions within the human protein C zymogen. The technique for modifying nucleotide sequences by site-directed mutagenesis is well known to those skilled in the art. See e.g., Sambrook, Fritsch & Maniatis, Molecular Cloning: A Laboratory Manual, second Edition (1989).

The human protein C derivatives can be made by techniques well known in the art utilizing eukaryotic cell lines, transgenic animals, or transgenic plants. Skilled artisans will readily understand that appropriate host eukaryotic cell lines include but are not limited to HepG2, LLC-MK$_2$, CHO-K1, 293, or AV12 cells, examples of which are described in U.S. Pat. No. 5,681,932, herein incorporated by reference. Furthermore, examples of transgenic production of recombinant proteins are described in U.S. Pat. Nos. 5,589,604 and 5,650,503, herein incorporated by reference.

Skilled artisans recognize that a variety of vectors are useful in the expression of a DNA sequence of interest in a eukaryotic host cell. Vectors that are suitable for expression in mammalian cells include, but are not limited to: pGT-h, pGT-d; pCDNA 3.0, pCDNA 3.1, pCDNA 3.1+Zeo, and pCDNA 3.1+Hygro (Invitrogen); and, pIRES/Hygro, and pIRES/neo (Clonetech). The preferred vector of the present invention is pIG3 as described in Example 2.

Other sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e. to maintain the proper reading frame.

The human protein C derivatives made by any of these methods must undergo post-translational modifications such as the addition of ten gamma-carboxy-glutamates, the addition of one erythro-beta-hydroxy-Asp (beta-hydroxylation), the addition of four Asn-linked oligosaccharides (glycosylation) and, the removal of the leader sequence (42 amino acid residues). Such post-translational modifications are necessary for efficient production and secretion of the protein C derivatives from mammalian cells.

It is known in the art that post-translational modifications of recombinant proteins such as the human protein C derivatives of the present invention may vary depending on which host cell line is utilized for the expression of the recombinant protein. For example, the post-translational modification of gamma-carboxylation, which is essential for the anti-coagulant activity of the human protein C derivatives of the present invention, may be higher, slightly lower, or much lower than plasma derived wild-type protein C gamma-carboxylation, depending on the host cell line used (Yan et al., Bio/Technology 8(7):655–661, 1990). Such differences in gamma-carboxylation provide a basis for the use of site-directed mutagenesis to change particular positions within the human protein C molecule that will result in an increase in anti-coagulant activity.

An embodiment of the present invention is increased production levels and increased specific activity of properly gamma-carboxylated protein C and/or protein C with increased anti-coagulant activity and resistance to serpin inactivation obtained by the inhibition of phosphorylation of the serine residue at position 12 as described in Example 1. This inhibition of phosphorylation can be accomplished by replacing the serine residue at position 12 with a non-phosphorylatable amino acid by site-directed mutagenesis, i.e. an amino acid other than Ser, Tyr, or Thr, or by the inhibition of the kinase responsible for the phosphorylation of the serine residue at position 12, for example, by including a non-toxic kinase inhibitor in the tissue-culture medium used to grow the host cell line.

Thus, an embodiment of the present invention is a human protein C derivative with increased anti-coagulant activity and resistance to serpin inactivation compared to wild-type activated protein C produced by the process comprising: transforming a host cell with a vector containing nucleic acid encoding a human protein C derivative; culturing said host cell in a medium appropriate for expression of said human protein C derivative; isolating said human protein C derivative from the culture medium; and activating said human protein C derivative.

Methods for the activation of zymogen forms of human protein C and human protein C derivatives to activated human protein C and activated human protein C derivatives are old and well known in the art. Human protein C may be activated by thrombin alone, by a thrombin/thrombomodulin complex, by RVV-X, a protease from Russell's Viper venom, by pancreatic trypsin or by other proteolytic enzymes.

Additionally, the present invention further relates to the treatment of acute coronary syndromes comprising myocardial infarction and unstable angina with aPC derivatives with increased anti-coagulation activity and resistance to serpin inactivation as compared to wild-type aPC.

The recombinant human protein C derivatives of the present invention are also useful for the treatment of thrombotic disorders such as stroke, abrupt closure following angioplasty or stent placement, and thrombosis as a result of peripheral vascular surgery.

Additionally, the recombinant human protein C derivatives of the present invention are useful for the treatment of vascular occlusive disorders or hypercoagulable states associated with sepsis, disseminated intravascular coagulation, major trauma, major surgery, burns, adult respiratory distress syndrome, transplantations, deep vein thrombosis, heparin-induced thrombocytopenia, sickle cell disease, thalassemia, viral hemorrhagic fever, thrombotic thrombocytopenic purpura, and hemolytic uremic syndrome. In another embodiment, the recombinant human protein C derivatives of the present invention are useful for the treatment of sepsis in combination with bacterial permeability increasing protein. In yet another aspect of this invention the activated human protein C derivatives of the present invention are combined with an anti-platelet agent(s) to treat or prevent various thrombotic disorders.

The recombinant human protein C derivatives of the present invention are useful for the treatment of acute arterial thrombotic occlusion, thromboembolism, or stenosis in coronary, cerebral or peripheral arteries or in vascular grafts, in combination with a thrombolytic agent such as tissue plasminogen activator, streptokinase, and related compounds or analogs thereof.

In another embodiment, the recombinant human protein C derivatives of the present invention are useful for the treatment of sepsis in combination with tissue factor pathway inhibitor.

Another aspect of the invention comprises treating the diseases and conditions caused or resulting from protein C deficiency as defined herein. This aspect of the invention contemplates any and all modifications to any aPC molecule resulting in increased anti-coagulant activity and resistance to serpin inactivation as compared to wild-type aPC.

The human protein C derivatives can be formulated according to known methods to prepare a pharmaceutical composition comprising as the active agent an aPC derivative and a pharmaceutically acceptable bulking agent. For example, a desired formulation would be one that is a stable lyophilized product of high purity comprising a bulking agent such as sucrose, trehalose or raffinose; a salt such as sodium chloride or potassium chloride; a buffer such as sodium citrate, Tris acetate, or sodium phosphate, at a pH of about 5.5 to about 6.5; and an activated human protein C derivative.

The human aPC derivatives of the present invention can be administered at an appropriate dose level understood and appreciated in the art and determined by the attending physician evaluating the particular circumstances surrounding the case. Preferably, the amount of human aPC derivative administered will be from about 0.01 µg/kg/hr to about 50 µg/kg/hr. More preferably, the amount of human aPC derivative administered will be about 0.1 µg/kg/hr to about 25 µg/kg/hr. Yet even more preferably the amount of human aPC derivative administered will be about 0.1 µg/kg/hr to about 15 µg/kg/hr. Even more preferably the amount of human aPC derivative administered will be about 1 µg/kg/hr to about 15 µg/kg/hr. The most preferable amounts of human aPC derivative administered will be about 5 µg/kg/hr or about 10 µg/kg/hr.

Preferably, the human aPC derivatives will be administered parenterally to ensure delivery into the bloodstream in an effective form by injecting a dose of 0.01 mg/kg/day to about 1.0 mg/kg/day, one to six times a day, for one to ten days. More preferably, the human aPC derivatives will be administered B.I.D. (2 times a day) for three days.

Alternatively, the human aPC derivatives will be administered at a dose of about 0.01 µg/kg/hr to about 50 µg/kg/hr, by continuous infusion for 1 to 240 hours.

The preferred plasma ranges obtained from the amount of human protein C derivative administered will be 0.02 ng/ml to less than 100 ng/ml.

In another alternative, the human aPC derivative will be administered by injecting a portion (⅓ to ½) of the appropriate dose per hour as a bolus injection over a time from about 5 minutes to about 120 minutes, followed by continuous infusion of the appropriate dose for up to 240 hours.

In another alternative, the human aPC derivative will be administered by local delivery through an intracoronary catheter as an adjunct to high-risk angioplasty (with and without stenting, and with or without combination therapy with anti-platelet agents). The amount of human aPC derivative administered will be from about 0.01 mg/kg/day to about 1.0 mg/kg/day by continuous infusion, bolus injection, or a combination thereof.

In yet another alternative, the human aPC derivatives will be administered subcutaneously at a dose of 0.01 mg/kg/day to about 1.0 mg/kg/day, to ensure a slower release into the bloodstream. Formulation for subcutaneous preparations will be done using known methods to prepare such pharmaceutical compositions.

The phrase "in combination with" as used herein, refers to the administration of additional agents with aPC either simultaneously, sequentially or a combination thereof. Examples of additional agents are anti-platelet agents, thrombolytic agents, and BPI protein.

The human aPC derivatives described in this invention have substantially increased anti-coagulant activity and increased plasma half-life compared to the wild-type human aPC. Therefore, these compounds will require either less frequent administration and/or smaller dosage. Finally, superior increases in human aPC derivative anti-coagulant activity and resistance to serpin inactivation may be achieved via two to six amino acid substitutions, which are less likely to be immunogenic than aPC derivatives with more than three amino acid substitutions.

The following Examples are provided merely to further illustrate the present invention. The scope of the invention shall not be construed as merely consisting of the following Examples.

EXAMPLE 1

Protein C Derivative Construction and Production

Human protein C derivatives were constructed using the polymerase chain reaction (PCR) following standard methods The source of the wild-type coding sequence was plasmid pLPC (*Bio/Technology* 5:1189–1192, 1987). The universal PCR primers used include: PC001b; 5'-GCGATG <u>TCTAGA</u>ccaccATGTGGCAGCTCACAAGCCTCCTGC-3', which encodes for an XbaI restriction site (underlined) used for subcloning, a Kozak consensus sequence (lowercase)

(Kozak, *J Cell Biol* 108(2):229–41, 1989), and the 5' end of the coding region for protein C: PC002E; 5'-CAGGGA TGATCACTAAGGTGCCCAGCTCTTCTGG-3', which encodes for the 3' end of the coding region for human protein C, and includes a BclI restriction site (underlined) for subcloning. All site-directed mutagenesis was accomplished by established PCR methodology, using complementary oligonucleotides containing the desired sequence changes. The first round of PCR was used to amplify two fragments of the protein C gene; the 5' fragment was generated using PC001b and the antisense mutagenic primer, and the 3' fragment was generated using PC002e and the sense mutagenic primer. The resulting amplified products were purified by standard procedures. These fragments were combined and then used as a template for a second round of PCR using primers PC001b and PC002e. The final PCR product was digested with XbaI and BclI and subcloned into similarly digested expression vector pIG3. A wild-type construct was similarly generated by PCR using the two universal primers and the plasmid pLPC as the template, followed by subcloning into pIG3. The mutations were confirmed by DNA sequencing of both the coding and non-coding strands. The pIG3 vector was generated by the insertion of an "internal ribosome entry site" (IRES) (Jackson, et al., *Trends Biochem Sci* 15(12):447–83, 1990) and green fluorescent protein (GFP) (Cormack, et al., *Gene* 173:33–38, 1996) gene into the mammalian expression vector pGTD (Gerlitz, et al., *Biochem J* 295(Pt 1):131–40, 1993). When a cDNA of interest is cloned into the multiple cloning site of pIG3, the GBMT promoter (Berg, et al., *Nucleic Acids Res* 20(20):5485–6, 1992) drives expression of a bicistronic mRNA (5'-cDNA-IRES-GFP-3'). Efficient translation of the first cistron is initiated by classical assembly of ribosome subunits on the 5'-methylated cap structure of the mRNA; while the normally inefficient translation of a second cistron is overcome by the IRES sequence which allows for internal ribosome assembly on the mRNA. The coupling of the cDNA and reporter on a single mRNA, translated as separate proteins, allows one to screen for the highest-producing clones on the basis of fluorescence intensity. The expression vector also contains an ampicillin resistance cassette for maintenance of the plasmid in *E. coli*, and a murine DHFR gene with appropriate expression sequences for selection and amplification purposes in mammalian tissue expression.

The adenovirus-transformed Syrian hamster AV12–664 cell line was grown in Dulbecco's modified Eagle's medium supplemented with 10% fetal bovine serum, 50 µg/mL gentamicin, 200 µg/mL Geneticin (G418), and 10 µg/mL vitamin K1. One day prior to transfection, cells were plated at a density of about $10^5$ cells/25 cm$^2$. FspI-linearized plasmids were transfected using either the calcium phosphate method (ProFection, Gibco BRL-Life Technologies) or FuGene-6 (Boehringer Mannheim), following the manufacturer's instructions. Approximately 48 hours after transfection, the medium was replaced with medium containing 250 nM methotrexate for selection. Colonies resistant to methotrexate were pooled 2–3 weeks after applying drug selection and expanded. The pools were subjected to fluorescence activated cell sorting based upon GFP fluorescence intensity (Cormack, 1996), with the most intense 5% of fluorescent cells being retained and expanded. To obtain material for purification, recombinant cells were grown in a modified mixture of Dulbecco's modified Eagle's and Ham's F-12 media (1:3) containing 1 µg/mL human insulin, 1 µg/mL human transferrin, and 10 µg/mL vitamin K1. Conditioned media were collected, adjusted to a final concentration of 5 mM benzamidine and 5 mM EDTA, pH 8.0, and protein C was purified via anion-exchange chromatography as described (Yan, et al., *Bio/Technology* 8:655–661, 1990). Purified protein was desalted/concentrated in Ultrafree-CL 30,000 NMWL filtration units (Millipore) using Buffer A (150 mM NaCl, 20 mM Tris-HCl, pH 7.4), and quantitated by Pierce BCA assay using bovine serum albumin (BSA) as the standard.

EXAMPLE 2

Serpin Resistant Mutants

The use of site-directed mutagenesis to change particular positions within human protein C molecule that decrease inactivation by serpins, and consequently result in extended plasma half-lives is described. The recognition sequences in the two primary aPC inhibitors $\alpha_1$-AT and PCI reveal some differences that can be exploited by altering the residues in aPC that interact with these sequences. Table I depicts the sequences recognized by aPC. The cleavage site occurs between the two residues shown in italics. Residues occupying the specific subsites, S2, S3', and S4', are underlined.

In general, the recognized sites in Factor Va are different from the sites in either Factor VIIIa or the inhibitors, therefore, it is possible to engineer the active site of aPC to preferentially cleave the more critical coagulant Factor Va, while at the same time decrease aPC's likelihood of being inhibited by serpins.

TABLE I

|  | S2' | S3'S4' |
|---|---|---|
| Coagulation Factors | | |
| Factor Va | 300–313 | N C P K K T R N L KK I T R |
| Factor Va | 500–513 | S R S L D R R G I QR A A A |
| Factor Va | 673–685 | S T V M A T R K M HD R L E |
| Factor VIIIa | 330–341 | P E E P Q L R M K NN E E A |
| Factor VIIIa | 560–571 | K E S V D Q R G N QI M S D |
| Serpins | | |
| PCI | | G T I F T F R S A RL N S Q |
| $\alpha_1$-AT | | F L E A I P M S I PP E V K |

In particular, three sites of recognition within the active site show distinctive differences between substrate recognition sequences and inhibitor recognition sequences: S2 (the $2^{nd}$ residue N-terminal to the cleavage site), S3' site, and S4'. The S2 site is primarily occupied by polar residues in the Factor Va sequences; unlike PCI and $\alpha_1$-AT, which have hydrophobic residues at this position. The S3' site occupied by polar side chains in all of the substrate sequences, but notably, a hydrophobic side chain in the $\alpha_1$-AT sequence. The S4' site is occupied by charged residues in all three Factor Va sequences, but is occupied by hydrophobic residues in the Factor VIIIa and inhibitor sequences.

Based upon the crystal structures of the PPACK-inhibited aPC (Mather, et al., *EMBO J.* 15(24):6822–6831, 1996) and Hirulog 3-inhibited thrombin (Qiu, et al., *Biochemistry* 31(47):11689–97, 1992), two aPC-substrate model structures were created and energy minimized using a CHARMm protocol:

(1) The sequence representing the Factor Va R506 cleavage sequence.

(2) The recognition sequence of $\alpha_1$-AT, with the Met substituted with Arg (corresponding to a polypeptide of $\alpha_1$-AT which exhibits extremely high affinity for aPC).

These models allowed for the identification of residues which form critical contacts in these three specific sites. A summary of residues which may form specific contacts within the active site, and replacements that are expected to provide enhanced specificity and/or activity are summarized in Table II. In general, mutations of residues that form contacts within the specific subsites of the active site are designed to reflect changes in the environment to drive the specificity of human aPC derivatives away from the recognition of the two primary physiological inhibitors, and potentially enhance human aPC derivative's proteolytic activity.

TABLE II

Mutations constructed for alteration of specificity

| Site | APC Residue | Constructed replacements | Substrate Contact |
|---|---|---|---|
| S2 | Thr254 | Ser | Aliphatic part of sidechain |
| S3' | Tyr302 | Glu, Gln | End of sidechain |
| S4' | Leu194 | Ser, Thr, Ala | Aliphatic part of sidechain |
| S4' | Ala195 | Gly | Aliphatic part of sidechain |
| S4' | Leu228 | Gln | End of sidechain |
| S4' | Phe316 | Asn | Aliphatic part of sidechain |

EXAMPLE 3

Activation of Recombinant Protein C

Complete activation of the zymogen forms of protein C and derivatives was accomplished by incubation with thrombin-sepharose. Thrombin-sepharose was washed extensively with Buffer A. 200 $\mu$L of packed thrombin-sepharose was mixed with 250 $\mu$g of protein C in 1 mL of the same buffer and incubated at 37° C. for four hours with gentle shaking on a rotating platform. During the course of the incubation, the degree of protein C activation was monitored by briefly pelleting the thrombin-sepharose, and assaying a small aliquot of the supernatant for aPC activity using the chromogenic substrate S-2366 (DiaPharma). Following complete activation, the thrombin-sepharose was pelleted, and the supernatant collected. aPC concentration was verified by Pierce BCA assay, and the aPC was either assayed directly, or frozen in aliquots at −80° C. All derivatives were analyzed by SDS-PAGE with either Coomassie-blue staining or Western Blot analysis to confirm complete activation (Laemmli, *Nature* 227:680–685, 1970).

EXAMPLE 4

Functional Characterization

The amidolytic activity of recombinant human aPC derivatives were determined by hydrolysis of the tri-peptide substrates S-2366 (Glu-Pro-Arg-p-nitroanilide), S-2238 (Pip-Pro-Arg-p-nitroanilide), and S-2288 (Ile-Pro-Arg-p-nitroanilide).

Assays were performed at 25° C., in Buffer A containing 1 mg $mL^{-1}$ BSA, 3 mM $CaCl_2$, and 0.5 nM aPC. Reactions (200 $\mu$L/well) were performed in a 96-well microtiter plate, and amidolytic activity was measured as the change in absorbance units/min at 405 nm as monitored in a ThermoMax kinetic micrometer plate reader. Kinetic constants were derived by fitting velocity data at varying substrate concentrations (16 $\mu$M to 2 mM) to the Michaelis-Menten equation. Changes in $A_{405}$ were converted to mmol product using a path length of 0.53 cm (Molecular Devices Technical Applications Bulletin 4-1), and an extinction coefficient for the released p-nitroanilide of 9620 $M^{-1}$ $cm^{-1}$ (Pfleiderer, *Methods Enzymol* 19:514–521, 1970). Anti-coagulant activity was assessed by measuring the prolongation of clotting time in the activated partial thromboplastin time clotting assay (Helena Laboratories). Clotting reactions were monitored in a ThermoMax kinetic microtiter plate reader, measuring the time to $V_{max}$ in the change in turbidity.

EXAMPLE 5

Inactivation of aPC Derivatives

The rates of inactivation of aPC derivatives were determined by incubating rabbit plasma or normal human plasma (Helena Labs) with 20 nM aPC (or derivatives) at 37° C. Plasma concentration was 90% (v/v) in the final reaction buffer containing 150 $\mu m^{-1}$ NaCl, 20 mM Tris, pH 7.4, and 1 mg $mL^{-1}$ BSA. Aliquots were removed at selected times, and activity was measured as amidolytic activity using S-2366 at a final concentration of 1 mM. The measured half-lives for aPC derivatives S11G:Q32E:N33D:L194S (GEDS), S11G:Q32E:N33D:L194S:T254S (GEDSS), H10Q:S11G:Q32E:N33D:L194S (QGEDS) and H10Q:S11G:Q32E:N33D:L194S:T254S (QGEDSS) are summarized in Table III.

TABLE III

| Variant | Inactivation in Plasma ($t_{1/2}$ Relative to wt) | |
|---|---|---|
| | Human | Rabbit |
| Wt | 1 x | 1 x |
| GED-S | 5.8 x | 8.5 x |
| GED-SS | 13 x | >20 x |
| QGED-S | 5.9 x | 8.5 x |
| QGED-SS | 8.5 x | >20 x |

EXAMPLE 6

In Vivo Pharmacokinetics

In vivo pharmacokinetic experiments were performed in normal rabbits to verify the observed in vitro effects in half-life as a result of the mutations. A marginal ear vein and a central ear artery was cannulated in the conscious rabbit. Activated protein C derivatives in buffer A (300 $\mu$g/ml) were used to administer a dose of 100 $\mu$g/Kg or 0.1 mg/kg bolus through the marginal ear vein catheter. Blood was sampled (0.45 ml) into a syringe containing 0.05 ml of 3.8% citrate containing benzamidine—adjustments were made to compensate for the syringe/needle dead space to yield the final concentration of 1 part citrate/benzamidine: 9 parts blood. Samples were collected 0, 2, 5, 10, 15, 30, 45, 60, 90, 120, 180, 240, 300 and 360 minutes post treatment, spun as soon as convenient after collection, and 200 $\mu$l of plasma was aliquoted into 96-well plates. The level of activated protein C derivatives were determined using an enzyme capture assay (ECA), as described previously (Gruber, et al., *Blood* 79(9):2340–2348, 1992), compared to standards ranging from 1 to 250 ng/mL diluted in pooled rabbit plasma.

Pharmacokinetic half-lifes for aPC derivatives S11G:Q32E:N33D:L194S (GEDS),

S11G:Q32E:N33D:L194S:T254S (GEDSS), H10Q:S11G:Q32E:N33D:L194S (QGEDS) and H10Q:S11G:Q32E:N33D:L194S:T254S (QGEDSS) following intravenous bolus administration in rabbits is shown in Table IV. The mean $T_{1/2}$ values indicate that all of the aPC derivatives have an increased half-life when compared to wild-type aPC.

TABLE IV

|  |  | 0.1 mg/kg | | | | | |
|---|---|---|---|---|---|---|---|
|  |  | 1 | 2 | 3 | Mean | SEM | N |
| WT | $T_{1/2}$(hour) | 0.17 | 0.31 | 0.18 | 0.2 | 0.04 | 3 |
| GEDS | $T_{1/2}$(hour) | 0.4 | 0.42 | 0.36 | 0.40 | 0.02 | 3 |
| GEDSS | $T_{1/2}$(hour) | 0.61 | 0.53 | 0.57 | 0.57 | 0.02 | 3 |
| QGEDS | $T_{1/2}$(hour) | 0.36 | 0.38 | 0.37 | 0.37 | 0.01 | 3 |
| QGEDSS | $T_{1/2}$(hour) | 0.57 | 0.65 | 0.44 | 0.54 | 0.06 | 3 |

EXAMPLE 7

Antithrombotic Efficacy in a Model of Thrombosis in the Rabbit

The arteriovenous (AV) shunt model of thrombosis is a frequently used and highly reproducible model of thrombosis which mimics the clinical conditions in which blood circulates through an artificial device such as a cardiopulmonary bypass machine or a kidney dialysis machine. In the anesthetized rabbit model of AV shunt thrombosis, blood is shunted for a fixed period from the carotid artery, through a 3-piece shunt of plastic tubing, to the jugular vein. The center section of tubing contains a thread upon which thrombotic material is deposited. While fibrin and platelets compose the thrombus, fibrin predominates. Antithrombotic efficacy was determined in the AV shunt model in the rabbit because the functional half-life of variants with modifications of the active-site is prolonged in the rabbit.

Human protein C derivatives with resistance to serpin inactivation and increased anti-coagulant activity as compared to wild-type activated protein C were evaluated. Each variant was infused for 75 minutes at a rate of 0.15 mg/Kg/hr. The 15-minute period of thrombosis occurred between 60 and 75 minutes. Blood was sampled for determination of aPTT and aPC concentration. The samples were analyzed for anticoagulant activity in whole blood, using aPTT, and for plasma concentration of aPC, using immunocapture and amidolytic activity.

The antithrombotic effect of an i.v. dose of 0.15 mg/Kg/hr was expressed as the average thrombus weight for each variant and for wild type (wt) aPC are summarized in Table V. The results demonstrate that the human protein C derivatives with resistance to serpin inactivation and increased anti-coagulant activity were more potent than wild type aPC.

TABLE V

| Derivative | Thrombus weight (mg) | (n) |
|---|---|---|
| Vehicle | 92.2 +/− 1.7 | (5) |
| Wt aPC | 97.5 +/− 1.6 | (4) |
| S11G:Q32E:N33D:L194S | 80.1 +/− 5.9 | (3) |
| S11G:Q32E:N33D:L194S:T254S | 67.6 +/− 10.7 | (4) |
| H10Q:S11G:Q32E:N33D:L194S | 73.8 +/− 6.6 | (4) |
| H10Q:S11G:Q32E:N33D:L194S:T254S | 70.1 +/− 3.5 | (4) |

What is claimed:

1. A human protein C derivative having, in its activated form, anticoagulating activity and resistance to inactivation by serpin, wherein said derivative comprises SEQ ID NO: 1 having an amino acid substitution for Leu at position 194 with an amino acid selected from the group consisting of Ser, Ala, Thr, His, Lys, Arg, Asn, Asp, Glu, Gly, and Gln, and having at least one additional amino acid substitution selected from the group consisting of:

His at position 10 is substituted with Gln; Ser at position 11 is substituted with Gly; Ser at position 12 is substituted with Lys; Gln at position 32 is substituted with Glu; Asn at position 33 is substituted with Asp or Phe; and the amino acid at position 195, 228, 249, 254, 302, or 316 is substituted with an amino acid selected from the group consisting of Ser, Ala, Thr, His, Lys, Leu, Mg, Asn, Asp, Glu, Gly, and Gln.

2. The human protein C derivative of claim 1 wherein said human protein C derivative is in its activated form.

3. A method of treating vascular occlusive disorders and hypercoagulable states, protein C deficiency, or acute coronary syndromes and disease states predisposing to thrombosis selected from the group consisting of myocardial infarction and unstable angina which comprises administering to a patient in need thereof a pharmaceutically effective amount of the human protein C derivative of claim 2.

4. A method of treating thrombotic disorders which comprises administering to a patient in need thereof a pharmaceutically effective amount of the human protein C derivative of claim 2 in combination with an anti-platelet agent.

5. A method of treating acute arterial thrombotic occlusion, thromboembolism, or stenosis in coronary, cerebral or peripheral arteries or in vascular grafts comprising:

administering to a patient in need thereof of pharmaceutically effective amount of the human protein C derivative of claim 2 in combination with a thrombolytic agent.

6. A pharmaceutical composition comprising: the human protein C derivative of claim 1 in a pharmaceutically acceptable diluent.

7. A pharmaceutical composition comprising: the human protein C derivative of claim 2 in a pharmaceutically acceptable diluent.

8. A human protein C derivative of claim 2, wherein the derivative is S11G:Q32E:N33D:L194S (SEQ ID NO: 3).

9. A human protein C derivative of claim 2, wherein the derivative is S11G:Q32E:N33D:L194S:T254S (SEQ ID NO: 4).

10. A human protein C derivative of claim 2, wherein the derivative is H10Q:S11G:Q32E:N33D:L194S (SEQ ID NO: 5).

11. A human protein C derivative of claim 2, wherein the derivative is H10Q:S11G:Q32E:N33D2L194S:T254S (SEQ ID NO: 6).

12. The method of claim 3 wherein said human protein C derivative is S11G:Q32E:N33D:L194S (SEQ ID NO: 3).

13. The method of claim 3 wherein said human protein C derivative is S11G:Q32E:N33D:L194S:T254S (SEQ ID NO: 4).

14. The method of claim 3 wherein said human protein C derivative is H10Q:S11G:Q32E:N33D:L194S (SEQ ID NO: 5).

15. The method of claim 3 wherein said human protein C derivative is H10Q:S11G:Q32E:N33D2L194S:T254S (SEQ ID NO: 6).

16. The method of claim 4 wherein said human protein C derivative is S11G:Q32E:N33D:L194S (SEQ ID NO: 3).

17. The method of claim 4 wherein said human protein C derivative is S11G:Q32E:N33D:L194S:T254S (SEQ ID NO: 4).

18. The method of claim 4 wherein said human protein C derivative is H10Q:S11G:Q32E:N33D:L194S (SEQ ID NO: 5).

19. The method of claim 4 wherein said human protein C derivative is H10Q:S11G:Q32E:N33D2L194S:T254S (SEQ ID NO: 6).

20. The method of claim 5 wherein said human protein C derivative is S11G:Q32E:N33D:L194S (SEQ ID NO: 3).

21. The method of claim 5 wherein said human protein C derivative is S11G:Q32E:N33D:L194S:T254S (SEQ ID NO: 4).

22. The method of claim 5 wherein said human protein C derivative is H10Q:S11G:Q32E:N33D:L194S (SEQ ID NO: 5).

23. The method of claim 5 wherein said human protein C derivative is H10Q:S11G:Q32E:N33D2L194S:T254S (SEQ ID NO: 6).

* * * * *

SEQUENCE LISTING

```
<160> NUMBER OF SEQ ID NOS: 12

<210> SEQ ID NO 1
<211> LENGTH: 419
<212> TYPE: PRT
<213> ORGANISM: Homo sapiens

<400> SEQUENCE: 1

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125
```

-continued

```
Asp Leu Leu Gln Cys His Pro Ala Val Lys Phe Pro Cys Gly Arg Pro
            130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro
```

<210> SEQ ID NO 2
<211> LENGTH: 461
<212> TYPE: PRT
<213> ORGANISM: Homo sapiens

<400> SEQUENCE: 2

```
Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
    50                  55                  60

Asp Phe Glu Glu Ala Lys Glu Ile Phe Gln Asn Val Asp Asp Thr Leu
65                  70                  75                  80
```

-continued

```
Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
        355                 360                 365

Pro His Asn Glu Cys Ser Glu Val Met Ser Asn Met Val Ser Glu Asn
370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
450                 455                 460
```

<210> SEQ ID NO 3
<211> LENGTH: 419
<212> TYPE: PRT
<213> ORGANISM: Homo sapiens

<400> SEQUENCE: 3

```
Ala Asn Ser Phe Leu Glu Glu Leu Arg His Gly Ser Leu Arg Glu
 1               5                  10                  15

Cys Ile Glu Glu Ile Cys Asp Phe Glu Ala Lys Glu Ile Phe Glu
                20                  25                  30

Asp Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
     50                  55                  60

Gly His Gly Thr Cys Ile Asp Gly Ile Gly Ser Phe Ser Cys Asp Cys
 65              70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
             100                 105                 110

Val Gly Trp Arg Arg Cys Ser Cys Ala Pro Gly Tyr Lys Leu Gly Asp
             115                 120                 125

Asp Leu Leu Gln Cys His Pro Ala Val Lys Phe Pro Cys Gly Arg Pro
 130                 135                 140

Trp Lys Arg Met Glu Lys Lys Arg Ser His Leu Lys Arg Asp Thr Glu
 145                 150                 155                 160

Asp Gln Glu Asp Gln Val Asp Pro Arg Leu Ile Asp Gly Lys Met Thr
                 165                 170                 175

Arg Arg Gly Asp Ser Pro Trp Gln Val Val Leu Leu Asp Ser Lys Lys
             180                 185                 190

Lys Ser Ala Cys Gly Ala Val Leu Ile His Pro Ser Trp Val Leu Thr
             195                 200                 205

Ala Ala His Cys Met Asp Glu Ser Lys Lys Leu Leu Val Arg Leu Gly
 210                 215                 220

Glu Tyr Asp Leu Arg Arg Trp Glu Lys Trp Glu Leu Asp Leu Asp Ile
 225                 230                 235                 240

Lys Glu Val Phe Val His Pro Asn Tyr Ser Lys Ser Thr Thr Asp Asn
                 245                 250                 255

Asp Ile Ala Leu Leu His Leu Ala Gln Pro Ala Thr Leu Ser Gln Thr
             260                 265                 270

Ile Val Pro Ile Cys Leu Pro Asp Ser Gly Leu Ala Glu Arg Glu Leu
             275                 280                 285

Asn Gln Ala Gly Gln Glu Thr Leu Val Thr Gly Trp Gly Tyr His Ser
 290                 295                 300

Ser Arg Glu Lys Glu Ala Lys Arg Asn Arg Thr Phe Val Leu Asn Phe
 305                 310                 315                 320

Ile Lys Ile Pro Val Val Pro His Asn Glu Cys Ser Glu Val Met Ser
                 325                 330                 335

Asn Met Val Ser Glu Asn Met Leu Cys Ala Gly Ile Leu Gly Asp Arg
             340                 345                 350

Gln Asp Ala Cys Glu Gly Asp Ser Gly Gly Pro Met Val Ala Ser Phe
             355                 360                 365

His Gly Thr Trp Phe Leu Val Gly Leu Val Ser Trp Gly Glu Gly Cys
 370                 375                 380

Gly Leu Leu His Asn Tyr Gly Val Tyr Thr Lys Val Ser Arg Tyr Leu
 385                 390                 395                 400

Asp Trp Ile His Gly His Ile Arg Asp Lys Glu Ala Pro Gln Lys Ser
                 405                 410                 415
```

Trp Ala Pro

<210> SEQ ID NO 4
<211> LENGTH: 419
<212> TYPE: PRT
<213> ORGANISM: Homo sapiens

<400> SEQUENCE: 4

```
Ala Asn Ser Phe Leu Glu Glu Leu Arg His Gly Ser Leu Glu Arg Glu
1               5                   10                  15

Cys Ile Glu Glu Ile Cys Asp Phe Glu Glu Ala Lys Glu Ile Phe Glu
            20                  25                  30

Asp Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65              70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Ser Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Ser Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365
```

```
His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 5
<211> LENGTH: 419
<212> TYPE: PRT
<213> ORGANISM: Homo sapiens

<400> SEQUENCE: 5

Ala Asn Ser Phe Leu Glu Glu Leu Arg Gln Gly Ser Leu Glu Arg Glu
1               5                   10                  15

Cys Ile Glu Glu Ile Cys Asp Phe Glu Glu Ala Lys Glu Ile Phe Glu
                20                  25                  30

Asp Val Asp Asp Thr Leu Ala Phe Trp Ser Lys His Val Asp Gly Asp
                35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
                180                 185                 190

Lys Ser Ala Cys Gly Ala Val Leu Ile His Pro Ser Trp Val Leu Thr
    195                 200                 205

Ala Ala His Cys Met Asp Glu Ser Lys Lys Leu Leu Val Arg Leu Gly
210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
                260                 265                 270

Ile Val Pro Ile Cys Leu Pro Asp Ser Gly Leu Ala Glu Arg Glu Leu
            275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320
```

-continued

```
Ile Lys Ile Pro Val Val Pro His Asn Glu Cys Ser Glu Val Met Ser
            325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 6
<211> LENGTH: 419
<212> TYPE: PRT
<213> ORGANISM: Homo sapiens

<400> SEQUENCE: 6

Ala Asn Ser Phe Leu Glu Glu Leu Arg Gln Gly Ser Leu Glu Arg Glu
1               5                   10                  15

Cys Ile Glu Glu Ile Cys Asp Phe Glu Glu Ala Lys Glu Ile Phe Glu
            20                  25                  30

Asp Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
        50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
            165                 170                 175

Arg Arg Gly Asp Ser Pro Trp Gln Val Val Leu Leu Asp Ser Lys Lys
        180                 185                 190

Lys Ser Ala Cys Gly Ala Val Leu Ile His Pro Ser Trp Val Leu Thr
    195                 200                 205

Ala Ala His Cys Met Asp Glu Ser Lys Lys Leu Leu Val Arg Leu Gly
        210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Ser Asp Asn
            245                 250                 255

Asp Ile Ala Leu Leu His Leu Ala Gln Pro Ala Thr Leu Ser Gln Thr
            260                 265                 270
```

-continued

```
Ile Val Pro Ile Cys Leu Pro Asp Ser Gly Leu Ala Glu Arg Glu Leu
            275                 280                 285
Asn Gln Ala Gly Gln Glu Thr Leu Val Thr Gly Trp Gly Tyr His Ser
        290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Glu Val Met Ser
                325                 330                 335
Asn Met Val Ser Glu Asn Met Leu Cys Ala Gly Ile Leu Gly Asp Arg
            340                 345                 350
Gln Asp Ala Cys Glu Gly Asp Ser Gly Gly Pro Met Val Ala Ser Phe
        355                 360                 365
His Gly Thr Trp Phe Leu Val Gly Leu Val Ser Trp Gly Glu Gly Cys
    370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro
```

<210> SEQ ID NO 7
<211> LENGTH: 1260
<212> TYPE: DNA
<213> ORGANISM: Homo sapiens

<400> SEQUENCE: 7

```
gccaactcct tcctggagga gctccgtcac agcagcctgg agcgggagtg catagaggag    60
atctgtgact cgaggaggc caaggaaatt ttccaaaatg tggatgacac actggccttc   120
tggtccaagc acgtcgacgg tgaccagtgc ttggtcttgc ccttggagca cccgtgcgcc   180
agcctgtgct gcgggcacgg cacgtgcatc gacggcatcg gcagcttcag ctgcgactgc   240
cgcagcggct gggagggccg cttctgccag cgcgaggtga gcttcctcaa ttgctcgctg   300
gacaacggcg gctgcacgca ttactgccta gaggaggtgg gctggcggcg ctgtagctgt   360
gcgcctggct acaagctggg ggacgacctc ctgcagtgtc accccgcagt gaagttccct   420
tgtgggaggc cctggaagcg gatggagaag agcgcagtc acctgaaacg agacacagaa   480
gaccaagaag accaagtaga tccgcggctc attgatggga gatgaccag gcggggagac   540
agccctggc agtggtcct gctggactca agaagaagc tggcctgcgg ggcagtgctc   600
atccacccct cctgggtgct gacagcggcc cactgcatgg atgagtccaa gaagctcctt   660
gtcaggcttg gagagtatga cctgcggcgc tgggagaagt gggagctgga cctggacatc   720
aaggaggtct tcgtccaccc caactacagc aagagcacca ccgacaatga catcgcactg   780
ctgcacctgg cccagcccgc caccctctcg cagaccatag tgcccatctg cctcccggac   840
agcggccttg cagagcgcga gctcaatcag gccggccagg agaccctcgt gacgggctgg   900
ggctaccaca gcagccgaga gaaggaggcc aagagaaacc gcaccttcgt cctcaacttc   960
atcaagattc ccgtggtccc gcacaatgag tgcagcgagg tcatgagcaa catggtgtct  1020
gagaacatgc tgtgtgcggg catcctcggg gaccggcagg atgcctgcga gggcgacagt  1080
ggggggccca tggtcgcctc cttccacggc acctggttcc tggtgggcct ggtgagctgg  1140
ggtgagggct gtgggctcct tcacaactac ggcgtttaca ccaaagtcag ccgctacctc  1200
gactggatcc atgggcacat cagagacaag gaagcccccc agaagagctg ggcaccttag  1260
```

<210> SEQ ID NO 8
<211> LENGTH: 1386
<212> TYPE: DNA
<213> ORGANISM: Homo sapiens

<400> SEQUENCE: 8

```
atgtggcagc tcacaagcct cctgctgttc gtggccacct ggggaatttc cggcacacca      60
gctcctcttg actcagtgtt ctccagcagc gagcgtgccc accaggtgct gcggatccgc     120
aaacgtgcca actccttcct ggaggagctc cgtcacagca gcctggagcg ggagtgcata     180
gaggagatct gtgacttcga ggaggccaag gaaattttcc aaaatgtgga tgacacactg     240
gccttctggt ccaagcacgt cgacggtgac cagtgcttgg tcttgccctt ggagcacccg     300
tgcgccagcc tgtgctgcgg gcacggcacg tgcatcgacg gcatcggcag cttcagctgc     360
gactgccgca gcggctggga gggccgcttc tgccagcgcg aggtgagctt cctcaattgc     420
tcgctggaca acggcggctg cacgcattac tgcctagagg aggtgggctg gcggcgctgt     480
agctgtgcgc ctggctacaa gctggggac gacctcctgc agtgtcaccc cgcagtgaag     540
ttcccttgtg ggaggccctg gaagcggatg gagaagaagc gcagtcacct gaaacgagac     600
acagaagacc aagaagacca agtagatccg cggctcattg atgggaagat gaccaggcgg     660
ggagacagcc cctggcaggt ggtcctgctg gactcaaaga gaagctggc ctgcggggca     720
gtgctcatcc accccctcctg ggtgctgaca gcggcccact gcatggatga gtccaagaag     780
ctccttgtca ggcttggaga gtatgacctg cggcgctggg agaagtggga gctggacctg     840
gacatcaagg aggtcttcgt ccaccccaac tacagcaaga gcaccaccga caatgacatc     900
gcactgctgc acctggccca gcccgccacc ctctcgcaga ccatagtgcc catctgcctc     960
ccggacagcg gccttgcaga gcgcgagctc aatcaggccg ccaggagac cctcgtgacg    1020
ggctggggct accacagcag ccgagagaag gaggccaaga gaaaccgcac cttcgtcctc    1080
aacttcatca gattcccgt ggtcccgcac aatgagtgca gcgaggtcat gagcaacatg    1140
gtgtctgaga acatgctgtg tgcgggcatc ctcggggacc ggcaggatgc ctgcgagggc    1200
gacagtgggg ggcccatggt cgcctccttc cacggcacct ggttcctggt gggcctggtg    1260
agctggggtg agggctgtgg gctccttcac aactacggcg tttacaccaa agtcagccgc    1320
tacctcgact ggatccatgg gcacatcaga gacaaggaag ccccccagaa gagctgggca    1380
ccttag                                                                 1386
```

<210> SEQ ID NO 9
<211> LENGTH: 1386
<212> TYPE: DNA
<213> ORGANISM: Homo sapiens

<400> SEQUENCE: 9

```
atgtggcagc tcacaagcct cctgctgttc gtggccacct ggggaatttc cggcacacca      60
gctcctcttg actcagtgtt ctccagcagc gagcgtgccc accaggtgct gcggatccgc     120
aaacgtgcca actccttcct ggaggagctc cgtcacggga gcctggagcg ggagtgcata     180
gaggagatct gtgacttcga ggaggccaag gaaattttcg aagatgtgga tgacacactg     240
gccttctggt ccaagcacgt cgacggtgac cagtgcttgg tcttgccctt ggagcacccg     300
tgcgccagcc tgtgctgcgg gcacggcacg tgcatcgacg gcatcggcag cttcagctgc     360
gactgccgca gcggctggga gggccgcttc tgccagcgcg aggtgagctt cctcaattgc     420
tctctggaca acggcggctg cacgcattac tgcctagagg aggtgggctg gcggcgctgt     480
```

```
agctgtgcgc ctggctacaa gctgggggac gacctcctgc agtgtcaccc cgcagtgaag    540
ttcccttgtg ggaggccctg gaagcggatg gagaagaagc gcagtcacct gaaacgagac    600
acagaagacc aagaagacca gtagatccg cggctcattg atgggaagat gaccaggcgg     660
ggagacagcc cctggcaggt ggtcctgctg gactcaaaga agaagtccgc ctgcggggca    720
gtgctcatcc accctcctg ggtgctgaca gcggcccact gcatggatga gtccaagaag     780
ctccttgtca ggcttggaga gtatgacctg cggcgctggg agaagtggga gctggacctg    840
gacatcaagg aggtcttcgt ccaccccaac tacagcaaga gcaccaccga caatgacatc    900
gcactgctgc acctggccca gcccgccacc ctctcgcaga ccatagtgcc catctgcctc    960
ccggacagcg gccttgcaga gcgcgagctc aatcaggccg ccaggagac cctcgtgacg    1020 ggctggggct accacagcag ccgagagaag gaggccaaga gaaaccgcac cttcgtcctc   1080
aacttcatca agattcccgt ggtcccgcac aatgagtgca gcgaggtcat gagcaacatg   1140
gtgtctgaga acatgctgtg tgcgggcatc ctcgggggacc ggcaggatgc ctgcgagggc   1200
gacagtgggg ggcccatggt cgcctccttc cacggcacct ggttcctggt gggcctggtg   1260
agctggggtg agggctgtgg gctccttcac aactacggcg tttacaccaa agtcagccgc   1320
tacctcgact ggatccatgg gcacatcaga gacaaggaag ccccccagaa gagctgggca   1380
ccttag                                                               1386

<210> SEQ ID NO 10
<211> LENGTH: 1386
<212> TYPE: DNA
<213> ORGANISM: Homo sapiens

<400> SEQUENCE: 10
atgtggcagc tcacaagcct cctgctgttc gtggccacct ggggaatttc cggcacacca     60
gctcctcttg actcagtgtt ctccagcagc gagcgtgccc accaggtgct gcggatccgc    120
aaacgtgcca actccttcct ggaggagctc cgtcacggga gcctggagcg ggagtgcata    180
gaggagatct gtgacttcga ggaggccaag gaaattttcg aagatgtgga tgacacactg    240
gccttctggt ccaagcacgt cgacggtgac cagtgcttgg tcttgccctt ggagcacccg    300
tgcgccagcc tgtgctgcgg gcacggcacg tgcatcgacg gcatcggcag cttcagctgc    360
gactgccgca cgggctggga gggccgcttc tgccagcgcg aggtgagctt cctcaattgc    420
tctctggaca cgcggctg cacgcattac tgcctagagg aggtgggctg gcggcgctgt    480
agctgtgcgc ctggctacaa gctgggggac gacctcctgc agtgtcaccc cgcagtgaag    540
ttcccttgtg ggaggccctg gaagcggatg gagaagaagc gcagtcacct gaaacgagac    600
acagaagacc aagaagacca gtagatccg cggctcattg atgggaagat gaccaggcgg     660
ggagacagcc cctggcaggt ggtcctgctg gactcaaaga agaagtccgc ctgcggggca    720
gtgctcatcc accctcctg ggtgctgaca gcggcccact gcatggatga gtccaagaag     780
ctccttgtca ggcttggaga gtatgacctg cggcgctggg agaagtggga gctggacctg    840
gacatcaagg aggtcttcgt ccaccccaac tacagcaaga gcaccagcga caatgacatc    900
gcactgctgc acctggccca gcccgccacc ctctcgcaga ccatagtgcc catctgcctc    960
ccggacagcg gccttgcaga gcgcgagctc aatcaggccg ccaggagac cctcgtgacg    1020 ggctggggct accacagcag ccgagagaag gaggccaaga gaaaccgcac cttcgtcctc   1080
aacttcatca agattcccgt ggtcccgcac aatgagtgca gcgaggtcat gagcaacatg   1140
```

| | |
|---|---|
| gtgtctgaga acatgctgtg tgcgggcatc ctcggggacc ggcaggatgc ctgcgagggc | 1200 |
| gacagtgggg ggcccatggt cgcctccttc cacggcacct ggttcctggt gggcctggtg | 1260 |
| agctggggtg agggctgtgg gctccttcac aactacggcg tttacaccaa agtcagccgc | 1320 |
| tacctcgact ggatccatgg gcacatcaga gacaaggaag cccccagaa gagctgggca | 1380 |
| ccttag | 1386 |

<210> SEQ ID NO 11
<211> LENGTH: 1386
<212> TYPE: DNA
<213> ORGANISM: Homo sapiens

<400> SEQUENCE: 11

| | |
|---|---|
| atgtggcagc tcacaagcct cctgctgttc gtggccacct ggggaatttc cggcacacca | 60 |
| gctcctcttg actcagtgtt ctccagcagc gagcgtgccc accaggtgct gcggatccgc | 120 |
| aaacgtgcca actccttcct ggaggagctc cgtcaaggga gcctggagcg ggagtgcata | 180 |
| gaggagatct gtgacttcga ggaggccaag gaaattttcg aagatgtgga tgacacactg | 240 |
| gccttctggt ccaagcacgt cgacggtgac cagtgcttgg tcttgccctt ggagcacccg | 300 |
| tgcgccagcc tgtgctgcgg gcacggcacg tgcatcgacg gcatcggcag cttcagctgc | 360 |
| gactgccgca cgggctggga gggccgcttc tgccagcgcg aggtgagctt cctcaattgc | 420 |
| tctctggaca cggcggctg cacgcattac tgcctagagg aggtgggctg gcggcgctgt | 480 |
| agctgtgcgc ctggctacaa gctgggggac gacctcctgc agtgtcaccc cgcagtgaag | 540 |
| ttcccttgtg ggaggccctg gaagcggatg gagaagaagc gcagtcacct gaaacgagac | 600 |
| acagaagacc aagaagacca agtagatccg cggctcattg atgggaagat gaccaggcgg | 660 |
| ggagacagcc cctggcaggt ggtcctgctg gactcaaaga agaagtccgc ctgcggggca | 720 |
| gtgctcatcc accctcctg ggtgctgaca gcggcccact gcatggatga gtccaagaag | 780 |
| ctccttgtca ggcttggaga gtatgacctg cggcgctggg agaagtggga gctggacctg | 840 |
| gacatcaagg aggtcttcgt ccaccccaac tacagcaaga gcaccaccga caatgacatc | 900 |
| gcactgctgc acctggccca gccgccacc ctctcgcaga ccatagtgcc catctgcctc | 960 |
| ccggacagcg gccttgcaga gcgcgagctc aatcaggccg ccaggagac cctcgtgacg | 1020 |
| ggctgggggct accacagcag ccgagagaag gaggccaaga gaaaccgcac cttcgtcctc | 1080 |
| aacttcatca agattcccgt ggtcccgcac aatgagtgca gcgaggtcat gagcaacatg | 1140 |
| gtgtctgaga acatgctgtg tgcgggcatc ctcggggacc ggcaggatgc ctgcgagggc | 1200 |
| gacagtgggg ggcccatggt cgcctccttc cacggcacct ggttcctggt gggcctggtg | 1260 |
| agctggggtg agggctgtgg gctccttcac aactacggcg tttacaccaa agtcagccgc | 1320 |
| tacctcgact ggatccatgg gcacatcaga gacaaggaag cccccagaa gagctgggca | 1380 |
| ccttag | 1386 |

<210> SEQ ID NO 12
<211> LENGTH: 1386
<212> TYPE: DNA
<213> ORGANISM: Homo sapiens

<400> SEQUENCE: 12

| | |
|---|---|
| atgtggcagc tcacaagcct cctgctgttc gtggccacct ggggaatttc cggcacacca | 60 |
| gctcctcttg actcagtgtt ctccagcagc gagcgtgccc accaggtgct gcggatccgc | 120 |
| aaacgtgcca actccttcct ggaggagctc cgtcaaggga gcctggagcg ggagtgcata | 180 |

```
gaggagatct gtgacttcga ggaggccaag gaaattttcg aagatgtgga tgacacactg      240
gccttctggt ccaagcacgt cgacggtgac cagtgcttgg tcttgccctt ggagcacccg      300
tgcgccagcc tgtgctgcgg gcacggcacg tgcatcgacg gcatcggcag cttcagctgc      360
gactgccgca gcggctggga gggccgcttc tgccagcgcg aggtgagctt cctcaattgc      420
tctctggaca acggcggctg cacgcattac tgcctagagg aggtgggctg gcggcgctgt      480
agctgtgcgc ctggctacaa gctgggggac gacctcctgc agtgtcaccc cgcagtgaag      540
ttcccttgtg ggaggccctg gaagcggatg gagaagaagc gcagtcacct gaaacgagac      600
acagaagacc aagaagacca agtagatccg cggctcattg atgggaagat gaccaggcgg      660
ggagacagcc cctggcaggt ggtcctgctg gactcaaaga agaagtccgc ctgcggggca      720
gtgctcatcc acccctcctg ggtgctgaca gcggcccact gcatggatga gtccaagaag      780
ctccttgtca ggcttggaga gtatgacctg cggcgctggg agaagtggga gctggacctg      840
gacatcaagg aggtcttcgt ccaccccaac tacagcaaga gcaccagcga caatgacatc      900
gcactgctgc acctggccca gcccgccacc tctcgcagaccatagtgcc catctgcctc      960 ccggacagcg gccttgcaga gcgcgagctc aatcaggccg gccaggagac cctcgtgacg     1020
ggctggggct accacagcag ccgagagaag gaggccaaga gaaaccgcac cttcgtcctc     1080
aacttcatca agattcccgt ggtcccgcac aatgagtgca gcgaggtcat gagcaacatg     1140
gtgtctgaga acatgctgtg tgcgggcatc ctcggggacc ggcaggatgc ctgcgagggc     1200
gacagtgggg ggcccatggt cgcctccttc cacggcacct ggttcctggt gggcctggtg     1260
agctggggtg agggctgtgg gctccttcac aactacggcg tttacaccaa agtcagccgc     1320
tacctcgact ggatccatgg gcacatcaga gacaaggaag cccccagaa gagctgggca      1380 ccttag                                                               1386
```